US011703952B2

(12) United States Patent
He et al.

(10) Patent No.: US 11,703,952 B2
(45) Date of Patent: Jul. 18, 2023

(54) SYSTEM AND METHOD FOR ASSISTING OPERATOR ENGAGEMENT WITH INPUT DEVICES

(71) Applicant: INTUITIVE SURGICAL OPERATIONS, INC., Sunnyvale, CA (US)

(72) Inventors: Xingchi He, San Jose, CA (US); Brandon D. Itkowitz, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/954,230

(22) Filed: Sep. 27, 2022

(65) Prior Publication Data
US 2023/0019316 A1    Jan. 19, 2023

Related U.S. Application Data

(63) Continuation of application No. 17/147,386, filed on Jan. 12, 2021, now Pat. No. 11,500,472, which is a
(Continued)

(51) Int. Cl.
*G06F 3/01* (2006.01)
*B25J 9/16* (2006.01)
*G06F 3/0346* (2013.01)

(52) U.S. Cl.
CPC ............ *G06F 3/017* (2013.01); *B25J 9/1628* (2013.01); *B25J 9/1664* (2013.01); *B25J 9/1674* (2013.01);
(Continued)

(58) Field of Classification Search
CPC ........ G06F 3/017; G06F 3/014; G06F 3/0346; G06F 3/011; G06F 3/013; B25J 9/1664;
(Continued)

(56) References Cited

U.S. PATENT DOCUMENTS 10,921,897 B2    2/2021    He et al.
2009/0027330 A1  1/2009    Aida
(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Andrey Belousov
(74) *Attorney, Agent, or Firm* — Artegis Law Group, LLP

(57) ABSTRACT

Systems and methods of assisting operator engagement with input devices include an input device configured to be operated by a hand of an operator, a repositionable structure coupled to the input device, a hand detection system, and a control unit. The control unit is configured to detect a position and an orientation of the hand using the hand detection system, determine, based on the position of the hand, a target position for the input device, wherein moving the input device from a current position of the input device to the target position moves the input device closer to a grasping position for the hand, and in response to determining that an orientation difference between the orientation of the hand and a current orientation of the input device is not greater than a threshold orientation difference, cause one or more actuators to move the input device toward the target position.

20 Claims, 6 Drawing Sheets

Related U.S. Application Data continuation of application No. 16/249,722, filed on Jan. 16, 2019, now Pat. No. 10,921,897.

(60) Provisional application No. 62/618,933, filed on Jan. 18, 2018.

(52) U.S. Cl.
CPC .............. *G06F 3/011* (2013.01); *G06F 3/013* (2013.01); *G06F 3/014* (2013.01); *G06F 3/0346* (2013.01)

(58) Field of Classification Search
CPC ...... B25J 9/1674; B25J 9/1628; B25J 9/1689; G05B 2219/39451; A61B 34/37
See application file for complete search history.

(56) References Cited

U.S. PATENT DOCUMENTS

| | | |
|---|---|---|
| 2012/0071892 A1 | 3/2012 | Itkowitz et al. |
| 2016/0066815 A1 | 3/2016 | Mei et al. |
| 2016/0375923 A1 | 12/2016 | Schulz et al. |
| 2021/0132701 A1 | 5/2021 | He et al. |

SYSTEM AND METHOD FOR ASSISTING OPERATOR ENGAGEMENT WITH INPUT DEVICES

RELATED APPLICATIONS

This application is a continuation of U.S. patent application Ser. No. 17/147,386 filed Jan. 12, 2021, which is a continuation of U.S. patent application Ser. No. 16/249,722 filed Jan. 16, 2019, and claims priority to and benefit of U.S. Provisional Patent Application No. 62/618,933, filed Jan. 18, 2018, and entitled "System and Method for Assisting Operator Engagement with Input Devices," each of which is incorporated by reference herein in its entirety.

TECHNICAL FIELD

The present disclosure relates generally to control of devices with repositionable arms and more particularly to assisting operator engagement with input devices.

BACKGROUND

More and more devices are being replaced with autonomous and semiautonomous electronic devices. This is especially true in industrial, entertainment, educational, and other settings. As a medical example, the hospitals of today with large arrays of autonomous and semiautonomous electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more repositionable arms and/or end effectors. It is also common to control the electronic devices using one or more input devices located at a user control system to control the motion and/or operation of the repositionable arms and/or the end effectors. When the electronic device is operated remotely from the user control system and/or the end effectors are being used in an area not directly visible to the operator, such as during computer-assisted operations where the end effectors are hidden by other materials or are out of the field of view, the electronic device may display cues to the operator using a display system. To aid the operator in controlling the repositionable arms and/or the end effectors, it is helpful to maintain alignment between a position and/or orientation, relative to the operator, of each input device used by the operator to manipulate an associated repositionable arm and/or end effector and a position and/or orientation of the associated end effector relative to an imaging device providing images of the associated end effector to the operator. This helps to provide the operator with an intuitive control over the associated end effector when relative motions of the input device by the hand of the operator are implemented as corresponding motion in the associated end effector as viewed using the imaging device. Thus, the associated end effector appears to follow the movements of the hand of the operator.

In order for this alignment to be maintained, the operator may be constrained to engage with the input device using a hand position and/or orientation relative to the user control system that matches with the position and/or orientation of the input device relative to the imaging device. However, engagement between the hand of the operator and the input device may not always be straightforward, such as when the operator has an obstructed or partially obstructed view of the input device. In addition, the current position and/or alignment of the input device may not represent a good ergonomic and/or easy to grasp position and/or orientation of the input device relative to the current position and/or alignment of the hand.

Accordingly, improved methods and systems for assisting operator engagement with input devices are desirable.

SUMMARY

Consistent with some embodiments, a system includes an input device configured to be operated by a hand of an operator, a hand detection system, and a control unit. The control unit is configured to detect the hand of the operator using the hand detection system; in response to a trigger condition, command the input device to move from a first position to a second position; and in response to a signal indicating an input provided by the operator to the input device, command a motion of an end effector associated with the input device. The second position is closer to a grasping position for the hand than the first position is to the grasping position of the hand.

Consistent with some embodiments, a method includes detecting, by a control unit, a hand of an operator using a hand detection system; in response to a trigger condition, commanding, by the control unit, an input device to move from a first position to a second position; and in response to a signal indicating an input provided by the operator to the input device, commanding, by the control unit, a motion of an end effector associated with the input device. The second position is closer to a grasping position of the hand than the first position to the grasping position of the hand.

Consistent with some embodiments, a non-transitory machine-readable medium including a plurality of machine-readable instructions which when executed by one or more processors associated with an user control system are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Figure 1:
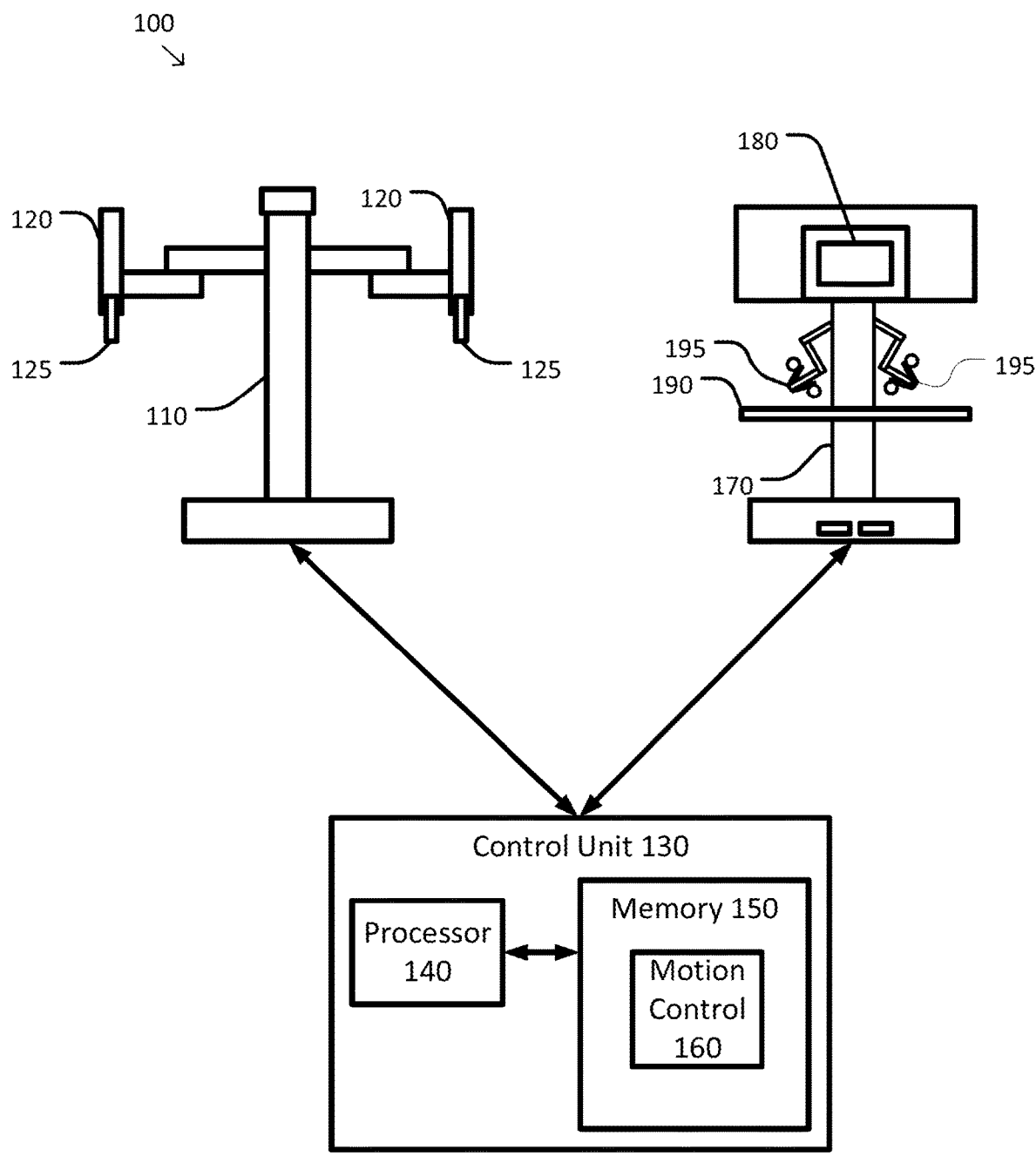
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of the devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the device and "distal" refers to a direction away from the base.

Aspects of the invention are described primarily in terms of an implementation using a da Vinci® Surgical System (specifically, a Model IS4000, marketed as the da Vinci® Xi™ Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000; the Model IS4200, commercialized as the da Vinci® X™ Surgical System) are merely exemplary and are not to be considered as limiting the scope of the inventive aspects disclosed herein. For example, any reference to surgical instruments and surgical methods is non-limiting as the instruments, systems, and methods described herein may be used for animals, human cadavers, animal cadavers, portions of human or animal anatomy, tissue removed from human or animal anatomies (without return to a human or animal anatomy), non-surgical diagnosis, industrial systems, and general robotic or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that includes, or does not include, surgical aspects.

FIG. 1 is a simplified diagram of a computer-assisted system 100 according to some embodiments. As shown in FIG. 1, computer-assisted system 100 includes a device 110 with one or more repositionable arms 120. Each of the one or more repositionable arms 120 may support one or more end effectors 125. In some examples, device 110 may be consistent with a computer-assisted surgical device. The one or more end effectors 125 may include instruments, imaging devices, and/or the like. In some medical examples, the instruments may include medical instruments, such as clamps, grippers, retractors, cautery tools, suction tools, suturing devices, and/or the like. In some medical examples, the imaging devices may include endoscopes, cameras, ultrasonic devices, fluoroscopic devices, and/or the like.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in control unit 130. Control unit 130 may be implemented as a stand-alone subsystem and/or as a board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control module 160 that may be used to support autonomous and/or semi-autonomous control of device 110 as is described in further detail below.

Control unit 130 may further be coupled to a user control system 170 via the interface. User control system 170 may be used by an operator, such as a surgeon, to control the movement and/or operation of the repositionable arms 120 and the end effectors 125. In some examples, user control system 170 may be an operator console, an operator workstation, and/or the like. To support operation of the repositionable arms 120, user control system 170 includes a display system 180 for displaying images of at least portions of one or more of the repositionable arms 120 and/or end effectors 125. For example, display system 180 may be used when it is impractical and/or impossible for the operator to see the repositionable arms 120 and/or the end effectors 125 as they are being used. User control system 170 may further include a workspace with one or more input devices 195 that may be used for operating the device 110, the repositionable arms 120, and/or the end effectors 125. Each of the input devices 195 may be coupled to the distal portion of their own repositionable arms so that movements of the input devices 195 may be detected by user control system 170 and communicated to control unit 130. To provide improved ergonomics, the workspace may also include one or more rests, such as an arm rest 190 on which operators may rest their arms while manipulating the input devices 195. In some examples, the display system 180 and the input devices 195 may be used by the operator to teleoperate the repositionable arms 120 and/or the end effectors 125. In some embodiments, device 110, user control system 170, and control unit 130 may correspond to a da Vinci® Surgical System commercialized by Intuitive Surgical, Inc. of Sunnyvale, Calif.

In some embodiments, other configurations and/or architectures may be used with computer-assisted system 100. In some examples, control unit 130 may be included as part of user control system 170 and/or device 110. In some embodiments, computer-assisted system 100 may be found in an operating room and/or an interventional suite. And although computer-assisted system 100 includes only one device 110 with two repositionable arms 120, one of ordinary skill would understand that computer-assisted system 100 may include any number of devices with repositionable arms and/or end effectors of similar and/or different design from device 110. In some examples, each of the devices may include fewer or more repositionable arms 120 and/or end effectors 125. Additionally, although user control system 170 includes only two input devices 195, one of ordinary skill would understand that user control system 170 may include any number of input devices as well as other input controls, sensors, and/or the like.

Motion control module 160 may support autonomous and/or semiautonomous control of device 110 using user control system 170. Motion control module 160 may additionally include one or more application programming interfaces (APIs) for receiving position, motion, and/or other sensor information from device 110 and/or user control system 170, exchanging position, motion, and/or collision avoidance information with other control units regarding other devices, and/or planning and/or assisting in the planning of motion for device 110, repositionable arms 120, end effectors 125, input devices 195, and/or the like. In addition, motion control module 160 may provide commands to one or more actuators used to control positions and/or orientations of repositionable arms 120, end effectors 125, input devices 195, and/or the like. And although motion control module 160 is depicted as a software module, motion control module 160 may be implemented using hardware, software, and/or a combination of hardware and software.

One of the tasks of motion control module 160 is to establish and maintain an alignment between the position and/or orientation of each of the input devices 195 and its associated end effector 125. This alignment may be established and maintained based on any appropriate reference or references appropriate to the system design. In some embodiments, the alignment of input device 195 relative to its associated end effector 125 is determined based on the orientation of input device 195 in an operator reference frame and the orientation of the associated end effector 125 in an imaging device reference frame. Input device 195 and its associated end effector 125 are considered to be aligned when their orientations are the same (or within a predetermined tolerance of each other) if the operator reference frame and imaging device reference frames are oriented in the same way. The operator reference frame may be defined by a part of the operator, something viewed by the operator, and/or the like. In some examples, the operator reference frame may be defined by the position and/or orientation of the eyes, head, torso, etc. of the operator. In some examples, the operator reference frame may be defined by the position and/or orientation of a head-mounted device, a viewer through which the operator looks through, a display configured to be viewed by the operator, and/or the like. In some examples, the imaging device reference frame may be defined by the distal portion of an imaging device, one or more imaging sensors of the imaging device, a field of view of the imaging device, and/or the like. In some medical examples, the imaging reference frame is defined by the field of view of an endoscope configured to capture images of the site of a medical procedure.

Another task of motion control module 160 is to assist the operator in engaging with one or more input devices 195. In some embodiments, this may include determining a position and/or orientation of each of the one or more input devices 195, determining a position and/or orientation of the hands of the operator, providing position and/or orientation cues to the operator to help the operator engage with the one or more input devices 195, move the one or more input devices 195 toward one or more hands of the operator, detect operator engagement with the one or more input devices 195, and/or the like as is discussed in further detail below.

Figure 2:
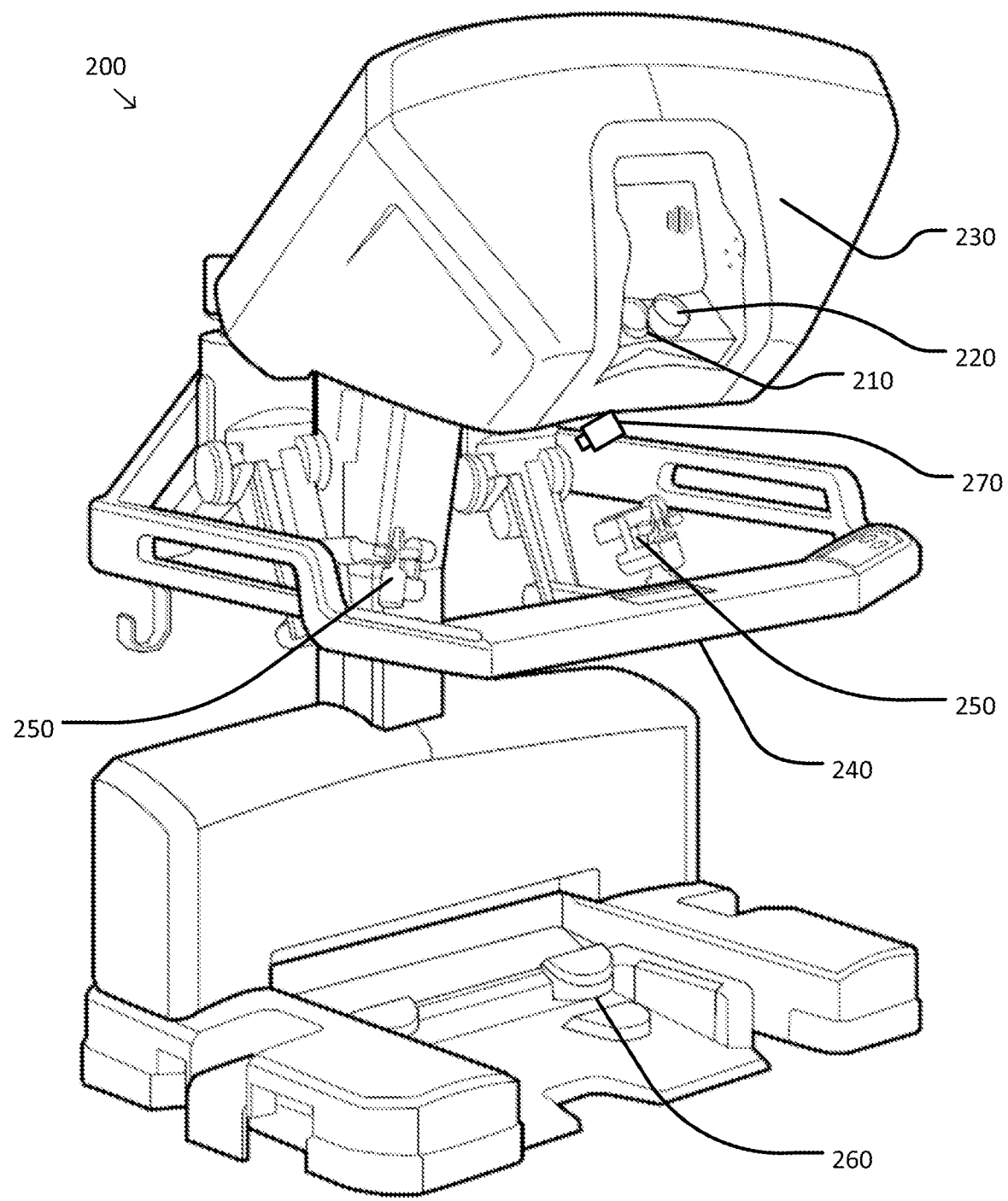
FIG. 2 is simplified diagram of a user control system according to some embodiments.

FIG. 2 is simplified diagram of a user control system 200 according to some embodiments. In some embodiments, user control system 200 is consistent with user control system 170. As shown in FIG. 2, user control system 200 is consistent with an operator console usable for controlling a computer-assisted device, such as computer-assisted device 110, using one or more input devices 195. Similar to user control system 170, user control system 200 includes a display system 210 for displaying images of at least portions of one or more tools and/or one or more end effectors, and a work site where the one or tools and/or the one or more end effectors are located. Display system 210 includes two viewing screens 220 for displaying left and right images that provide a stereoscopic view of the one or more tools, the one or more end effectors, and the work site. Display system 210 is located within a housing 230.

User control system 200 further includes an arm rest 240 and two input devices 250, which are consistent with arm rest 190 and input devices 195 of user control system 170, respectively. Input devices 250 are located at a distal portion of respective repositionable arms that allow the positions and/or orientations of input devices 250 to be independently monitored and/or controller. User control system 200 further includes additional input controls, such as a foot pedal 260.

One of the many advantages of user control system 200 is the ergonomic arrangement between its various elements. For example, display system is located a convenient head height for an operator sitting at user control system 200 and generally aligns a direction of view of the operator down toward the workspace where input devices 250 are located. Thus, as the operator uses input devices 250 to control one or more tools and/or one or more end effectors, the positions and/or orientations of the one or more tools and/or one or more end effectors in the images displayed on display system 210 appear aligned with the positions and/or orientations of the hands of the operator that are engaged with and manipulating input devices 250. This arrangement, which supports intuitive control of the one or more tools and/or one end effectors, however, may interfere with the ability of the operator to see and/or engage with input devices 250. In some examples, when the head of the operator is engaged with display system 210 to view the images displayed therein, the operator is not able to see input devices 250 and the hands operating input devices 250. In some examples, housing 230 may also interfere with the ability of the operator to see input devices 250 and the hands of the operator when the hands are in the vicinity of input devices 250.

To help address these issues, user control system further includes an imaging device 270 that is capable of capturing images of input devices 250 and the hands of the operator. In some examples, imaging device 270 may be mounted toward an underside of housing 230 with a field of view directed toward input devices 250. In some examples, imaging device 270 may be a imaging device with scanning and/or depth ranging capability, a red-green-blue-depth (RGBD) imaging device, a stereoscopic imaging device, and/or the like. In some examples, images captured by imaging device 270 may be displayed on display system 210 to provide the operator with a view of input devices 250 and the hands of the operator. In some examples, images from imaging device 270 may be further analyzed using imaging processing techniques to determine positions and/or orientations of the hands, detect one or more gestures made by the hands, and/or the like. In some examples, imaging device 270 may be replaced and/or supplemented with one or more infrared and/or ultrasonic ranging or proximity detectors, light walls, and/or the like (not shown) for detecting the hands, determining positions and/or orientations of the hands and/or fingers (which includes thumbs), detecting one or more gestures made by the hands, and/or the like. In some examples, images from imaging device 270 and/or information derived from the images may further be used to provide one or more position and/or orientation cues to aid the operator in engaging with input devices 250 as is described in further detail below. In some examples, imaging device 270 and/or one or more infrared and/or ultrasonic ranging or proximity detectors, light walls, and/or the like may collectively be part of a hand detection system.

Figure 3:
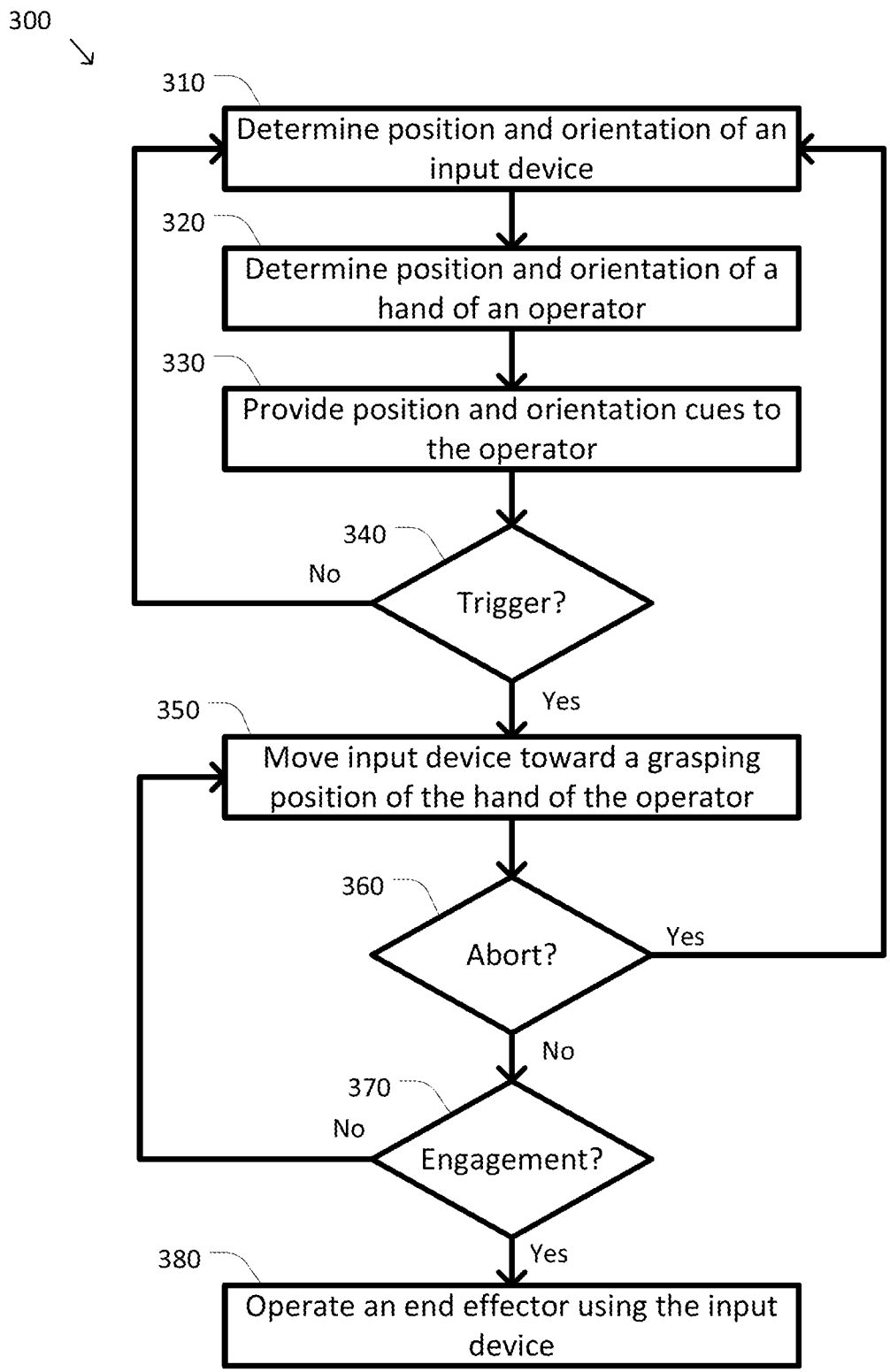
FIG. 3 is a simplified diagram of a method of assisting operator engagement with an input device according to some embodiments.

FIG. 3 is a simplified diagram of a method of assisting operator engagement with an input device according to some embodiments. One or more of the processes 310-380 of method 300 may be implemented, at least in part, in the form of executable code stored on non-transitory, tangible, machine-readable media that when run by one or more processors (e.g., the processor 140 in control unit 130) may cause the one or more processors to perform one or more of the processes 310-380. In some embodiments, method 300 may be performed by a module, such as motion control module 160. In some embodiments, method 300 may be used to assist an operator to engage with an input device, such as one of the input devices 195 and/or one of the input devices 250.

In some embodiments, one or more of the processes of method 300 may be performed in a different order than the order implied by the flow chart in FIG. 3. In some examples, processes 310 and 320 may be performed in any order and/or concurrently. In some examples, processes 310-330 may be performed concurrently with any of the processes 340-380. In some examples, processes 360 and 370 may be performed in any order and/or concurrently. In some examples, process 360 and/or 370 may be performed concurrently with process 350. In some examples, process 330 is optional and may be omitted.

At a process 310, a position and orientation of the input device to be engaged with by the operator is determined. In some examples, the position and orientation determined may be associated with a distal portion of the input device, which is to be grasped by the operator. In some examples, signals from one or more joint sensors in the input device and/or the repositionable arm to which the input device is coupled may be combined with one or more kinematic models of the input device and/or the repositionable arm to determine the position and orientation. In some examples, an imaging system, such as an imaging system including imaging device 270, may be used to determine the position and orientation of the input device by using one or more image processing techniques to recognize one or more fiducial markers on the input device, a shape of the input device, and/or the like. In some examples, position and orientation information provided by both the joint sensors and the imaging system may be used to determine the position and orientation of the input device. In some examples, the position and orientation of the input device may be constrained based on a position and/or orientation of a tool and/or end effector relative to an imaging device located in or near a work site where the tool and/or end effector is located.

At a process 320, a position and orientation of a hand of an operator is determined. In some examples, an imaging device, such as imaging device 270, is used to capture images of the hand and one or more image processing techniques are used to determine the position and orientation of the hand. In some examples, the position and orientation of the hand may include a position and orientation of one or more fingers and/or the thumb of the hand. In some examples, the one or more image processing techniques may include one or more of edge detection, shape detection, and/or the like. In some examples, one or more infrared and/or ultrasonic ranging or proximity detectors, light walls, and/or the like may replace and/or supplement the imaging device for determining the position and orientation of the hand and/or the one or more fingers.

At an optional process 330, one or more position and orientation cues are provided to the operator. In some examples, the one or more position and orientation cues may include one or more of display of live images of the input device and the hand, display of a virtual hand over live images of the end effector associated with the input device, a blended overlay of live images of the hand and/or the input device and live images of the end effector associated with the input device, a live virtual view of a virtual hand and a virtual input device, and/or the like. In some examples, multiple position and orientation cues may be displayed using a split screen display mode, and/or the like. In some examples, the one or more types of position and orientation cues to provide may be selected based on operator preference.

Figure 4:
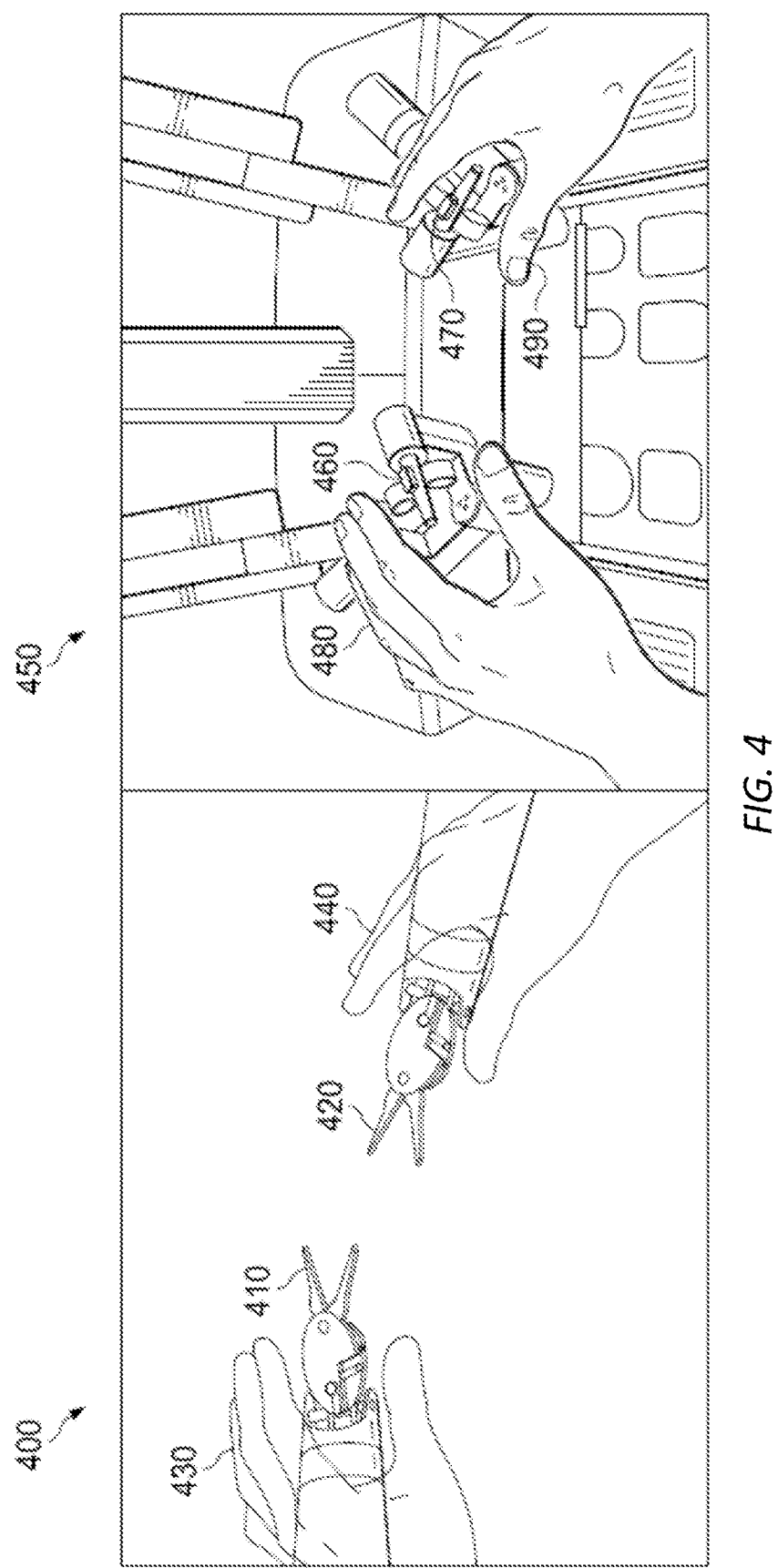
FIGS. 4-6 are simplified diagrams of user interfaces demonstrating position and orientation cues usable for assisting operator engagement with an input device according to some embodiments.

FIG. 4 is a simplified diagram of a user interface for providing position and orientation cues to an operator according to some embodiments. In some embodiments, the user interface may be displayed on a display system, such as display system 180 and/or 210. As shown in FIG. 4, a split screen display mode is shown with multiple types of position and orientation cues when method 300 is being performed for two input devices concurrently. On a left side of FIG. 4, a view 400 of a work site is shown with live images of two end effectors 410 and 420. Also shown in view 400 are virtual hands 430 and 440, which correspond to the left and right hands respectively, of the operator. On a right side of FIG. 4, a view 450 of a portion of a user control system, such as user control system 170 and/or 200, is shown with live images of two input devices 460 and 470. Also shown in view 450 are live images of the left hand 480 and the right hand 490 of the operator. Also shown in FIG. 4 is that the position and orientation of end effector 410 and input device 460 as well as the position and orientation of end effector 420 and input device 470 are generally matched, which is consistent with the intuitive control of end effectors 410 and 420 using input devices 460 and 470, respectively. As further shown in FIG. 4 is that the relative position and orientation of left and right hands 480 and 490 relative to input devices 460 and 470, respectively, match the position and orientation of virtual hands 430 and 440 relative to end effectors 410 and 420, respectively. Thus, FIG. 4 demonstrates how the position and orientation of input devices 460 and 470 relative to left and right hands 480 and 490, respectively, are used to determine the position and orientation of where the virtual hands 430 and 440 are rendered in view 400 relative to end effectors 410 and 420, respectively.

In some examples, the position and orientation of the input device (e.g., input device 460 and/or 470) determined during process 310 and the position and orientation of the hand (e.g., left hand 480 and/or right hand 490) determined during process 320 are used to determine the relative position and orientation of the input device (e.g., input device 460 and/or 470) and the hand (e.g., left hand 480 and/or right hand 490), which in turn is used to determine the position and orientation of the corresponding virtual hand (e.g., virtual hand 430 and/or 440) relative to the end effector (e.g., end effector 410 and/or 420) associated with the input device (e.g., input device 460 and/or 470).

Referring back to FIG. 3 and process 330, the one or more position and orientation cues may be different from those depicted in FIG. 4. In some examples, a view with both virtual end effectors and virtual hands may be used to replace and/or supplement view 400 and/or 450. In some examples, each of the virtual end effectors in the view may displayed in place of the corresponding end effector. In some examples, the position and orientation of each of the virtual end effectors may be determined based on the position and orientation of the corresponding end effector. In some examples, one or more techniques similar to those used to determine the position and orientation of the input device during process 310 may be used to determine the position and orientation of each of the end effectors relative to the imaging device in the work site used to obtain the images of the end effectors.

In some examples, a blended view of the work site with images of the end effectors with images of the hands of the operator may be used to replace and/or supplement view 400 and/or 450. In some examples, a technique like alpha blending may be used to create the blended view. In some examples, one or more filters, such as a depth-based filter, may be used to remove images of the input devices from the images of the hands of the operator.

At a process 340, it is determined whether a trigger condition activating further assistance in engaging with the input device is detected. In some examples, the trigger condition may include the detection of a gesture by the operator indicating that the operator is ready for further assistance. In some examples, the gesture may include opening of the hand and/or splaying the fingers indicating an open grip posture for the hand. In some examples, the gesture may be detected using one or more image processing techniques to detect the movement of the hand and/or a change in orientation of the fingers relative to the hand.

In some examples, the trigger condition may include detecting that the hand and/or a grasping position of the hand is, or has moved to be, closer to the input device than a threshold distance. In some examples, the threshold distance may be configured as any value between 5 and 50 cm, including 5 cm, 10 cm, 20.3 cm, 25 cm, 50 cm, or any value between 5 and 50 cm. In some examples, the images from the imaging device of the user control system and/or one or more hand and/or finger sensors may provide an indication of whether the hand of the operator is in proximity to the input device. In some examples, each of the one or more hand and/or finger sensors may provide a binary indication (e.g., the hand is near the input device), an analog indication (e.g., how close the hand is to the input device, or where the hand is relative to the input device), and/or a certainty level of whether the hand is near the input device. In some examples, evaluation of the input from the one or more hand and/or finger sensors may include performing one or more pattern and/or image processing techniques to make the binary, analog, and/or certainty level determination. In some examples, the one or more hand and/or finger sensors may include one or more infrared and/or ultrasonic ranging or proximity detectors, light walls, and/or the like.

In some examples, the trigger condition may include a voice command from the operator. In some examples, sound from a microphone on the user control system may be used to determine whether the operator speaks a key word or key phrase (e.g., "engage") that corresponds to the trigger condition. In some examples, the key word or key phrase may be selected by the operator.

In some examples, the trigger condition may be a gaze command from the operator. In some examples, a gaze tracking unit may detect the gaze command. In some examples, the gaze command may correspond to an eye action, such as two blinks in less than a threshold period of time, and/or the like. In some examples, the gaze command may include detecting that the operator is continuously looking at a specific target (e.g., a user interface element for triggering engagement and/or the like) for at least a threshold amount of time.

In some examples, the trigger condition may include detection of activation of one or more other input controls by the operator. In some examples, the one or more other input controls may include one or more of a pedal, a knee switch, an elbow switch, a pressure and/or contact sensor in an arm rest (e.g., arm rest 190 and/or arm rest 240), a head-in detection sensor associated with a display system (e.g., display system 180 and/or display system 210), and/or the like. In some examples, the choice of the one or more other input controls may be determined based on operator preference.

In some examples, process 340 may be configured to detect a trigger condition and/or a combination of trigger conditions selected from any of the trigger conditions herein described. In some examples, the choice of which trigger conditions are used may be configured based on operator preference. In some examples, a combination of two or more detected trigger conditions may be used to satisfy the trigger condition of process 340.

When a trigger condition is not detected, method 300 returns to process 310 where updated positions and orientations of the input device and/or the hand are determined and one or more updated position and orientation cues are optionally provided. When a trigger condition is detected, assisted engagement continues by moving the input device toward a grasping position of the hand of the operator using a process 350. In some examples, the grasping position may be based on the position and/or orientation of the hand detected during process 320. In some examples, the grasping position may be based on operator preference. In some examples, the grasping position may be based on an ergonomic center for the operator. In some examples, the ergonomic center for the operator may be determined as described in commonly-owned U.S. patent application Ser. No. 15/125,679, disclosing "System and Method for Recentering Imaging Devices and Input Controls," which is hereby incorporated by reference. In some examples, the detection of the trigger condition may include sending a notification to the operator. In some examples, the notification may include one or more of a message displayed on the display system, activating and/or flashing an indicator, an audio message and/or tone, haptic feedback, and/or the like.

At the process 350, the input device is moved toward a grasping position of the hand of the operator. Using the position and orientation of the input device determined during process 310 and the position and orientation of the hand determined during process 320 a motion that moves the distal portion of the input device toward a grasping position of the hand may be determined. In some examples, the motion may move the distal portion of the input device closer to the hand. In some examples, the motion may move the distal portion of the input device from a position that provides poorer ergonomics for grasping by the hand (e.g., a position located toward the back side of the hand, a position more proximal to the operator than the hand, such as at or above the wrist of the operator, and/or the like) to a position that provides better ergonomics for grasping by the hand (e.g., a position located toward the palm side of the hand, a position distal to the wrist, a position within range of the fingers of the hand, and/or the like). In some examples, the determined motion may be limited so that just the position of the distal portion of the input device is changed, but the orientation of the distal portion of the input device remains unchanged so that it remains matched to the orientation of the distal portion of the associated end effector. In some examples, when the orientation of the input device is not adjusted to the orientation of the hand, it is up to the operator to adjust the orientation of the hand to match the orientation of the input device, such as by using the one or more position and orientation cues provided by process 330.

At a process 360, it is determined whether an abort condition for the assisted engagement is detected. In some examples, one or more actions by the operator and/or conditions may occur, which indicate that the operator is no longer ready or interested in further assistance with the engagement process and that movement of the input device toward the hand of the operator should be aborted. In some examples, the abort condition may include the detection of a gesture by the operator indicating that the operator is no longer ready for further active assistance. In some examples, the gesture may include closing of the hand into a fist, raising of the palm in a stop gesture, and/or the like. In some examples, the gesture may be detected using one or more image processing techniques to detect the movement of the hand or a change in orientation of the fingers relative to the hand.

In some examples, the abort condition may include detecting that the hand and/or a grasping position of the hand has moved farther than a threshold distance away from the input device. In some examples, the threshold distance may be configured as any value between 5 cm and 50 cm including 5 cm, 10 cm, 20.3 cm, 25 cm, 50 cm, or any value between 5 and 50 cm. In some examples, the images from the imaging device of the user control system and/or one or more hand and/or finger sensors may provide an indication of whether the hand of the operator is moved away from proximity to the input device. In some examples, each of the one or more hand and/or finger sensors may provide a binary indication (e.g., the hand is near the input device), an analog indication (e.g., how close the hand is to the input device, or where the hand is relative to the input device), and/or a certainty level of whether the hand is near the input device. In some examples, evaluation of the input from the one or more hand and/or finger sensors may include performing one or more pattern and/or image processing techniques to make the binary, analog, and/or certainty level determination. In some examples, the one or more hand and/or finger sensors may include one or more infrared and/or ultrasonic ranging or proximity detectors, light walls, and/or the like.

In some examples, the abort condition may include a voice command from the operator. In some examples, sound from a microphone on the user control system may be used to determine whether the operator speaks a key word or key phrase (e.g., "abort", "stop", and/or the like) that corresponds to the abort condition. In some examples, the key word or key phrase may be selected by the operator.

In some examples, the abort condition may be a gaze command from the operator. In some examples, the gaze tracking unit may detect the gaze command. In some examples, the gaze command may correspond to an eye action, such as closing one or more eyes for at least a timeout period, two blinks of one or more eyes in less than a threshold period of time, and/or the like. In some examples, the gaze command may include detecting that the operator is continuously looking at a specific target (e.g., a user interface element for aborting engagement and/or the like) for at least a threshold period of time. In some examples, the gaze command may include detecting cessation of a gaze command, such as cession of a gaze command associated with the trigger condition.

In some examples, the abort condition may include detection of deactivation of one or more other input controls by the operator. In some examples, the one or more other input controls may include one or more of a pedal, a knee switch, an elbow switch, a pressure and/or contact sensor in an arm rest (e.g., arm rest 190 and/or arm rest 240), a head-in detection sensor associated with a display system (e.g., display system 180 and/or display system 210), and/or the like. In some examples, the choice of the one or more other input controls may be determined based on operator preference.

In some examples, the abort condition may correspond to a time-out occurring before engagement is detected by a process 370 (discussed below) and/or not detecting a recognizable gesture of the hand (e.g., one of the trigger condition gestures) before the time-out occurs. In some examples, a time-out timer may be started when the trigger condition is detected during process 340 and if the time-out timer expires before engagement is detected by process 370, then the abort condition is satisfied. In some examples, the duration of the time-out timer may be configured as any value in a range from 5 to 30 seconds, such as 5, 10.4, 20, or 30 seconds. In some examples, the choice of whether to use the time-out timer and/or the duration of the time-out timer may be set based on operator preference.

In some examples, the abort condition may include detecting that there is excessive misalignment between the orientation of the input device determined during process 310 and the orientation of the hand determined during process 320. In some examples, excessive misalignment may correspond to a difference in the orientations being larger than a threshold angular difference. In some examples, the difference in the orientations may be determined about any arbitrary axis. In some examples, the difference in the orientations may be determined as one or more difference components about a set of axes (e.g., roll, pitch, and/or yaw axes of the distal end of the input device, Euler angle axes, and/or the like). In some examples, the threshold angular difference may be different for each axis in the set of axes. In some examples, the threshold angular difference (or each threshold angular difference) may be set as any configurable angle selected from between 25 and 45 degrees (e.g., 25, 30, 40.5, or 45 degrees and/or the like). In some examples, the detected abort gesture may also include any gesture that results in the difference in orientation exceeding the threshold angular difference.

In some examples, the abort condition may be a fault condition of the system. In some examples, the fault condition is human triggered by activating a virtual or physical fault condition trigger, such as by interacting with a virtual button displayed on a graphical user interface or a physical emergency-stop button. In some examples, the fault condition is automatically triggered by the system in response to one or more detected system or operator abnormalities.

Figure 5:
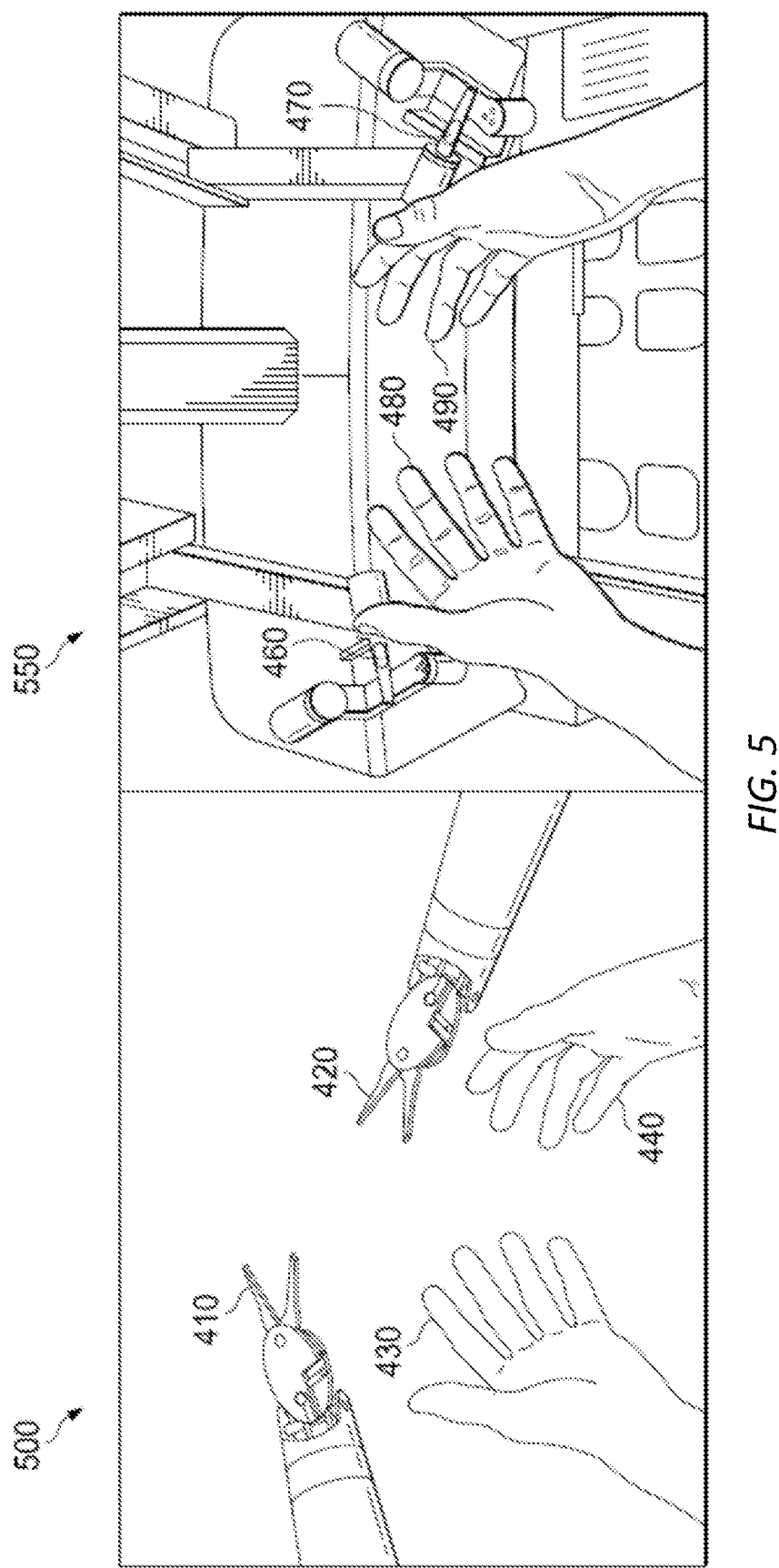

FIG. 5 is a simplified diagram of the user interface of FIG. 4 depicting an example of an abort condition corresponding to excessive misalignment according to some embodiments. Like FIG. 4, the user interface in FIG. 5 includes a view 500 of the work site with live images of end effectors 410 and 420 along with virtual hands 430 and 440 as well as a view 550 with live images of input devices 460 and 470 and hands 480 and 490. As shown in FIG. 5, hands 480 and 490 are rotated away from a suitable orientation for grasping input devices 460 and 470, respectively. This rotation away is also shown in the orientations of virtual hands 430 and 440 in view 400. This excessive misalignment does not make it practical for the hand of the operator to be engaged with the input device while still maintaining a match between the orientation of the input device and the orientation of the end effector that is associated with the input device.

Referring back to FIG. 3 and process 360, in some examples, process 360 may be configured to detect an abort condition and/or a combination of abort conditions selected from any of the abort conditions herein described. In some examples, the choice of which abort conditions are used may be configured based on operator preference. In some examples, a combination of two or more detected abort conditions may be used to satisfy the abort condition of process 360.

When an abort condition is not detected, assisted engagement continues with a process 370. When an abort condition is detected, movement of the input device toward the hand of the operator is ceased and method 300 returns to process 310 where updated positions and orientations of the input device and/or the hand are determined and one or more updated position and orientation cues are optionally provided in anticipation of another attempt at assisted engagement with the input device. In some examples, the detection of the abort condition may include sending a notification to the operator. In some examples, the notification may include one or more of a message displayed on the display system, activating and/or flashing an indicator, an audio message and/or tone, haptic feedback, and/or the like.

At the process 370, it is determined whether there is engagement between the hand of the operator and the input device. In some examples, when engagement is detected, this indicates that movement of the input device toward the hand of the operator should end and that control of the input device should switch to a mode where the input device is manipulated by the hand. Detection of the engagement between the hand of the operator and the input device corresponds to a detection that the hand is in contact with the input device, the hand is within close proximity of the input device, and/or the hand is interacting with the input device.

In some examples, when the input device includes one or more hand and/or finger sensors, the one or more hand and/or finger sensors may be used to detect contact by the hand with the input device and/or close proximity between the hand and the input device. In some examples, close proximity may correspond to the hand and/or the grasping position of the hand being closer than a threshold value or vector of values selected from any configurable value between 0.5 to 1.0 cm from the distal portion of the input device, including 0.5 cm, 0.6 cm, 1.0 cm, or any value in that range. Each of the one or more hand and/or finger sensors may provide an indication of whether the hand is in contact with and/or in close proximity to the input device. In some examples, each of the one or more hand and/or finger sensors may provide a binary indication (e.g., either: (a) the hand is in contact with or in close proximity to an input device or (b) the hand is not in contact with or in close proximity to the input device), an analog indication (e.g., how close the hand is to the input device, or where the hand is relative to the input device), and/or a certainty level of whether the hand is in contact with or in close proximity to the input device. In some examples, evaluation of the input from the one or more hand and/or finger sensors may include performing one or more pattern and/or image processing techniques to make the binary, analog, and/or certainty level determination. In some examples, each of the one or more hand and/or finger sensors may include a contact switch, a capacitive touch sensor, a pressure sensor, a force sensor, an infrared and/or ultrasonic ranging or proximity detector, a light wall, a capacitive proximity sensor, an inductive sensor, a RF sensor, an optical sensor, an imaging sensor, a vision device, and/or the like.

In some examples, differences between the position and orientation of the input device determined during process 310 and the position and orientation of the hand determined during process 320 may be used to detect when the hand is likely in contact with and/or in close proximity to the input device.

In some examples, a difference between an actual position and/or orientation of the input device and the commanded position and/or orientation of the input device may be used to indicate that engagement between the hand and the input device has occurred. For example, a difference that is greater than a threshold position difference and/or greater than a threshold angular difference may be used to indicate that engagement between the hand and the input device has occurred. As another example, a difference that is less than a threshold position difference and less than a threshold angular difference may be used to indicate that engagement between the hand and the input device has not occurred. A threshold position difference in some embodiments can be set as a single threshold distance in the range from 0.1 cm to 1.0 cm, including 0.1 cm, 0.3 cm, 1.0 cm, and any other value within the range. A threshold position difference can be set based on an estimate of a position difference associated with the hand engaging with the input device. A threshold position difference in some embodiments can include multiple threshold distances along different axes. A threshold angular difference in some embodiments can be set as any configurable value in the range from 1 degree to 10 degrees, including 1, 5, and 10 degrees about any axis. A threshold angular difference in some embodiments can include multiple threshold angles about different axes. A threshold angular difference can be set based on an estimate of an angular difference associated with the hand engaging with the input device. In some examples, the actual position and orientation of the input device may be the position and orientation determined during process 310. In some examples, the commanded position and orientation of the input device may be determined from the positional and/or rotational set points for each of the joints in the input device and the repositionable arm to which the input device is coupled and the one or more kinematic models of the input device and the repositionable arm.

Figure 6:
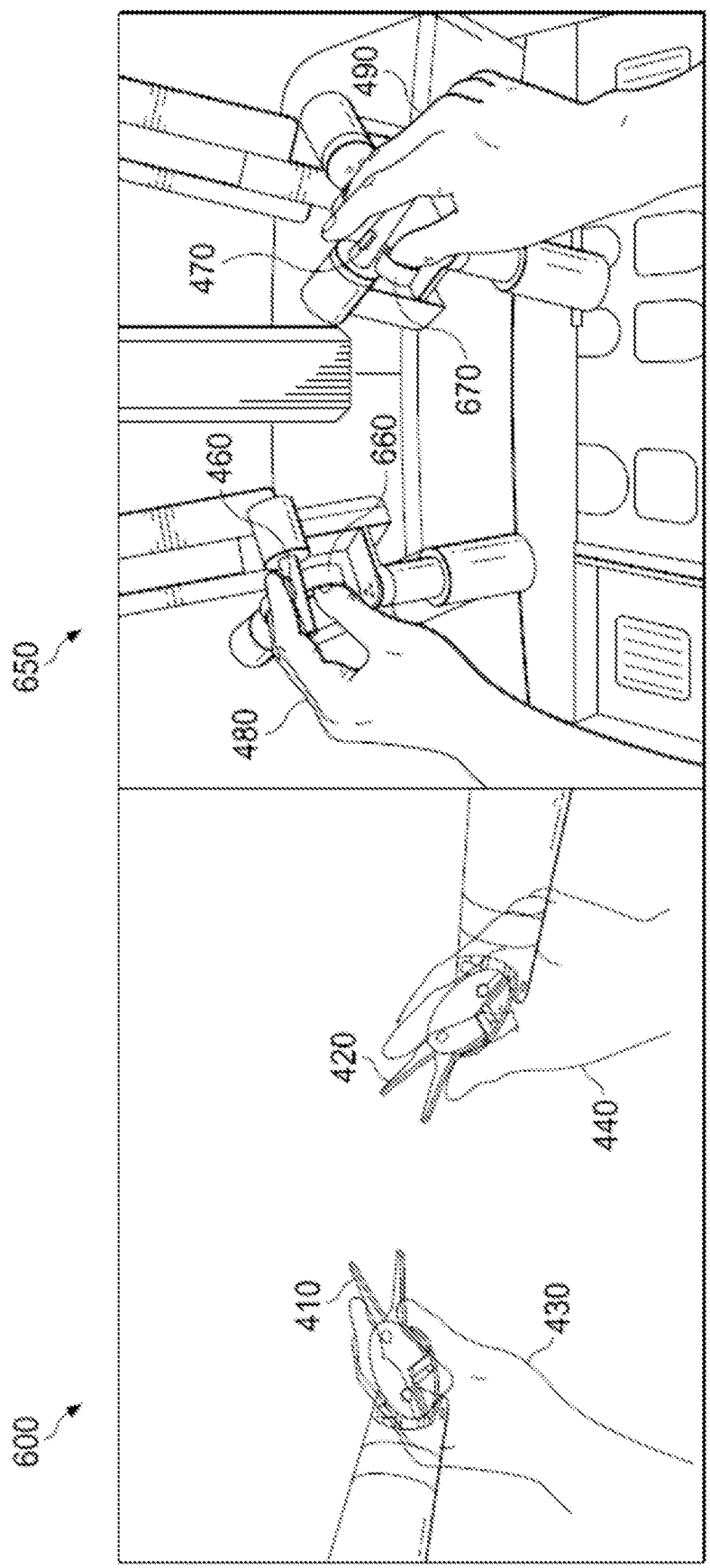

FIG. 6 is a simplified diagram of the user interface of FIG. 4 depicting an example of engagement between the hands of the operator and the input devices according to some embodiments. Like FIG. 4, the user interface in FIG. 6 includes a view 600 of the work site with live images of end effectors 410 and 420 along with virtual hands 430 and 440 as well as a view 650 with live images of input devices 460 and 470 and hands 480 and 490. As shown in FIG. 6, hands 480 and 490 are engaged with input devices 460 and 470, respectively, as noted by the physical contact between hands 480 and 490 with input devices 460 and 470, respectively, as well as the insertion of the thumbs in finger loops 660 and 670. This engagement is also shown in the positions and orientations of virtual hand 430 and 440, which coincide with the positions and orientations of end effectors 410 and 402, respectively, as shown in view 600.

Referring back to FIG. 3 and process 370, in some examples, process 370 may be configured to detect engagement using any combination of the one or more engagement detection approaches described herein. In some examples, the choice of which of the engagement detection approaches are used may be configured based on operator preference. In some examples, a combination of two or more engagement detection approaches may be used to determine engagement using process 360.

When engagement between the hand and the input device is detected, movement of the input device toward the hand of the operator ceases and the input device is used to control its associated end effector using a process 380. In some examples, the detection of engagement may include sending a notification to the operator. In some examples, the notification may include one or more of a message displayed on the display system, activating and/or flashing an indicator, an audio message and/or tone, haptic feedback, and/or the like. When engagement between the hand and the input device is not detected, movement of the input device toward the grasping position of the hand of the operator continues by returning to process 350.

At the process 380, the end effector associated with the input device is operated using the end effector. Once engagement between the hand and the input device is obtained, the hand is used to change the position and/or orientation of the distal portion of the input device. In some examples, the change in the position and/or orientation of the distal portion of the input device may be detected based on signals from one or more joint sensors of the input device and/or the repositionable arm to which the input device is couple indicating that the input device is being moved. In some examples, the change in the position and/or orientation of the distal portion of the input device is used to cause corresponding changes in the position and/or orientation of the end effector associated with the input device.

As discussed above and further emphasized here, FIG. 3 is merely an example which should not unduly limit the scope of the claims. One of ordinary skill in the art would recognize many variations, alternatives, and modifications. According to some embodiments, the processes of method 300 may be applied independently for each input device and/or in synchronization with the other input devices (i.e., so that engagement may occur concurrently between two input devices and both hands of the operator). In some examples, when method 300 is used concurrently for two input devices and two hands, the volume around the input devices and the hands may be partitioned into regions (e.g., left and right regions) with the concurrent methods 300 being applied separately for each region so that the engagement assistance for the input device in each respective region is provided relative to the hand closest to that region. In some examples, when method 300 is applied concurrently for two input devices, the one or more position and motion cues for each input device and hand may be combined into the same user interface and/or optionally provided in different regions of the split screen.

In some embodiments, method 300 may be adapted to assist in the engagement between different portions of the anatomy of the operator and/or different types of input devices. In some examples, the other portions of the anatomy of the operator include one or more of a foot, a knee, an elbow, a wrist, a forearm, a head, and/or the like. In some examples, the different types of input device may include one or more of a telestrator, a joy stick, a wrist or similar strap, and/or the like. In some examples, method 300 may be modified to adjust portions of the user control system, such as one or more of a height of the arm rest (e.g., arm rest 190 and/or arm rest 240), a height of a chair, a height or position of a display system (e.g., display system 180 and/or display system 210), and/or the like.

In some embodiments, processes 340 and 350 may be omitted and/or skipped when method 300 is performed. In some examples, when the operator does not desire further assistance in engaging with the input device using process 350, the operator may not issue the trigger condition and instead rely on just the one or more position and orientation cues provided during process 330 to move the hand into engagement with a stationary input device (which is detected by process 370) and/or terminate the assisted engagement using process 360.

In some embodiments, differences between the orientation of the input device and the orientation of the hand during process 350 that are below a threshold angular difference may be addressed by including a change in orientation of the input device with the motion that moves the input device toward the grasping position of the hand of the operator during process 350. In some examples, the threshold angular difference is set as any configurable angle selected from between 15 and 30 degrees (e.g., 15, 18.7, 20, 25, or 30 degrees and/or the like). In some examples, the change in orientation of the input device may include all the differences in the orientation or only part of the differences in the orientation. In some examples, the change in orientation of the input device may include changing the orientation of the input device to address a configurable percentage of the differences, such as 25 percent, 35 percent, 50, percent, 75 percent, 90 percent, and/or the link. In some examples, the change in orientation of the input device may include changing the orientation of the input device so that the differences are reduced to a configurable orientation difference, such as any angle between 5 and 25 degrees (e.g., 5, 10, 12.5, 150, 20, and 25 degrees). In some examples, the change in orientation of the input device may be corrected to the orientation of the end effector after engagement occurs by applying a corrective reorientation to the input device (and the hand of the operator) after engagement is detected during process 370 and before process 380 begins. In some examples, the change in orientation of the input device may be corrected gradually over time as the input device is used to operate the associated end effector during process 380 using a process called ratcheting. Techniques for ratcheting are further described in co-owned U.S. Pat. No. 8,423,186, disclosing "Ratcheting for Master Alignment of a Teleoperated Minimally-invasive Surgical Instrument," which is hereby incorporated by reference. In some embodiments, a combination of two or more of these techniques may be used to address differences between the orientation of the input device and the orientation of the hand.

In some embodiments, additional actions may be taken to further facilitate the engagement process. In some examples, a stiffness of the input device may be reduced during process 350 so that while engagement is being established between the hand of the operator and the input device, the input device will exhibit a compliant behavior. In some examples, the stiffness of the input device may be reduced by lowering one or more force and/or torque limits of one or more control algorithms used to control one or more actuators that cause the input device to move toward the grasping position of the hand of the operator during process 350. The reduced one or more force and/or torque limits give the distal portion of the input device a softer feel as the hand makes contact with the input device. In some examples, the stiffness may be reduced in a single step and/or reduced gradually using a ramp, an s-curve, a series of steps, and/or the like. In some examples, the stiffness of the input device may be increased back to normal levels during process 380.

As discussed above and further emphasized here, FIGS. 4-6 are merely examples which should not unduly limit the scope of the claims. One of ordinary skill in the art would recognize many variations, alternatives, and modifications. In some embodiments, virtual hands 430 and/or 440 as rendered in views 400, 500, and/or 600 may be rendered in different ways. In some examples, virtual hands 430 and/or 440 may be rendered using one or more of a solid outline, a dashed outline, a false color, an opacity, and/or the like. In some examples, virtual hands 430 and/or 440 may be blended with the images of end effectors 410 and/or 420 and other background elements using, for examples, alpha blending and/or the like.

In some embodiments, different arrangements, compositions, and position and orientation cues are possible. In some examples, just one of the views (e.g., the view of end effectors with virtual hands or the view of input devices and hands) may be provided. In some examples, the relative arrangement between the views in the split screen may be different (e.g., the view of input devices and hands may be shown to the left of the view of the end effectors with virtual hands). In some examples, the split screen may include three, four, or more views. In some examples, the split screen may be arranged horizontally, vertically, and/or tiled. In some examples, the position and orientation cues may be different from the position and orientation cues shown in FIGS. 4-6 and may include any of the position and orientation cues described with respect to process 330. In some examples, the content in the views may be filtered to remove content that may interfere with the engagement process. In some examples, the filtering may remove visual content that is further away from the respective imaging device than the relevant content (e.g., removing portions of the work site further away from the work site imaging device than the end effectors and/or removing portions of the user control system environment further away from the user control system imaging device than the distal portions of the input devices). In some examples, the views may include additional virtual content, such as virtual counterparts to portions of the end effectors that are occluded by objects, anatomy, and/or the like in the work site. In some examples, the views may be augmented to include one or more motion cues, such as directional, arrows indicating the one or more directions in which each of the input devices, hands, end effectors, and/or virtual hands are moving to assist engagement during process 350. In some examples, the one or more motion cues may include a planned motion trajectory for an input device so that the operator may anticipate where the input device is being moved during process 350.

Some examples of control units, such as control unit 130 may include non-transitory, tangible, machine readable media that include executable code that when run by one or more processors (e.g., processor 140) may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system comprising:
    an input device configured to be operated by a hand of an operator;
    a repositionable structure coupled to the input device, the repositionable structure comprising one or more actuators drivable to move the input device;
    a hand detection system; and
    a control unit configured to:
        detect a position of the hand using the hand detection system,
        determine, based on the position of the hand, a target position for the input device, wherein moving the input device from a current position of the input device to the target position moves the input device closer to a grasping position for the hand,
        detect an orientation of the hand using the hand detection system, and
        in response to determining that an orientation difference between the orientation of the hand and a current orientation of the input device is not greater than a threshold orientation difference, cause the one or more actuators to move the input device toward the target position.

2. The system of claim 1, wherein the control unit is further configured to, in response to determining that the orientation difference is greater than the threshold orientation difference:
    not cause the one or more actuators to move the input device toward the target position.

3. The system of claim 1, wherein the control unit is further configured to:
    in response to detecting an engagement of the hand with the input device, cause the one or more actuators to stop moving the input device toward the target position.

4. The system of claim 3, wherein the control unit is further configured to:
    detect whether the hand is engaged with the input device by detecting whether a position difference between an actual position of the input device and a commanded position of the input device is greater than a threshold position difference.

5. The system of claim 1, wherein the control unit is further configured to, in response to determining that the orientation difference is not greater than the threshold orientation difference, cause the one or more actuators to move the input device toward a target orientation, wherein moving the input device from the current orientation to the target orientation moves the input device closer to a grasping orientation for the hand.

6. The system of claim 5, wherein:
    the input device is associated with an end effector; and
    the control unit is further configured to:
        in response to detecting an engagement of the hand with the input device, cause the one or more actuators to move the input device from the target orientation toward an orientation based on an orientation of the end effector.

7. The system of claim 1, wherein:
    the input device is associated with an end effector; and
    the control unit is further configured to:
        after detecting an engagement of the hand with the input device, command a motion of the end effector based on an input received from the input device.

8. The system of claim 1, wherein the control unit is further configured to:
    detect a trigger condition before causing the one or more actuators to move the input device toward the target position;
    wherein the trigger condition comprises at least one event selected from the group consisting of:
        a predefined gesture of the hand;
        the hand being less than a threshold distance from the input device; and
        a predefined gaze command.

9. The system of claim 1, further comprising:
    a display system, wherein the control unit is further configured to provide on the display system at least one cue selected from the group consisting of:
        images of the hand and the input device;
        an image of an end effector indication and a virtual hand, the end effector indication comprising a view of an end effector or a view of a virtual end effector, the virtual hand being positioned and oriented in the image relative to the end effector indication based on a relative position and orientation between the hand and the input device; and
        an image blending an image of the hand with an image of the end effector.

10. The system of claim 1, wherein:
    the control unit is further configured to, in response to detecting an abort condition, cause the one or more actuators to stop moving the input device toward the target position; and
    to detect the abort condition the control unit is configured to:
        detect an abort gesture of the hand; or
        detect a lack of a recognizable gesture of the hand within a time-out period; or
        determine that a threshold period of time has elapsed without detecting that the hand is engaged with the input device; or
        detect that the hand is farther away than a threshold distance from the input device.

11. The system of claim 1, wherein the control unit is further configured to cause the one or more actuators to reduce an effective stiffness of the input device while causing the one or more actuators to move the input device toward the target position.

12. A method of operating a system comprising a repositionable structure, a hand detection system, and a control unit, wherein the repositionable structure comprises one or more actuators and is configured to support an input device, the method comprising:
   detecting, by the control unit using the hand detection system, a position of a hand of an operator;
      determining, by the control unit based on the position of the hand, a target position for the input device, wherein moving the input device from a current position of the input device to the target position moves the input device closer to a grasping position for the hand,
   detecting, by the control unit using the hand detection system, an orientation of the hand; and
   in response to determining that an orientation difference between the orientation of the hand and a current orientation of the input device is not greater than a threshold orientation difference, causing, by the control unit, the one or more actuators to move the input device toward the target position.

13. The method of claim 12, further comprising:
   in response to detecting an engagement of the hand with the input device, causing, by the control unit, the one or more actuators to stop moving the input device toward the target position.

14. The method of claim 12, further comprising:
   in response to determining that the orientation difference is not greater than the threshold orientation difference, causing, by the control unit, the one or more actuators to move the input device toward a target orientation, wherein moving the input device from the current orientation to the target orientation moves the input device closer to a grasping orientation for the hand.

15. The method of claim 14, wherein the input device is associated with an end effector, the method further comprising:
   in response to detecting an engagement of the hand with the input device, causing, by the control unit, the one or more actuators to move the input device from the target orientation toward an orientation based on an orientation of the end effector.

16. The method of claim 12, further comprising:
   detecting, by the control unit, a trigger condition before causing the one or more actuators to move the input device toward the target position;
   wherein detecting the trigger condition comprises detecting:
      a predefined gesture of the hand; or
      the hand being less than a threshold distance from the input device; or
      a predefined gaze command.

17. The method of claim 12, further comprising:
   in response to detecting an abort condition, causing, by the control unit, the one or more actuators to stop moving the input device toward the target position;
   wherein detecting the abort condition comprises:
      detecting an abort gesture of the hand; or
      detecting a lack of a recognizable gesture of the hand within a time-out period; or
      determining that a threshold period of time has elapsed without detecting that the hand is engaged with the input device; or
      detecting that the hand is farther away than a threshold distance from the input device.

18. The method of claim 12, further comprising causing the one or more actuators to reduce an effective stiffness of the input device while causing the one or more actuators to move the input device toward the target position.

19. A non-transitory machine-readable medium comprising a plurality of machine-readable instructions which, when executed by one or more processors associated with a user control system comprising a repositionable structure having one or more actuators and configured to support an input device, are adapted to cause the one or more processors to perform a method comprising:
   detecting, using a hand detection system, a position of a hand of an operator;
      determining, based on the position of the hand, a target position for the input device, wherein moving the input device from a current position of the input device to the target position moves the input device closer to a grasping position for the hand,
   detecting, using the hand detection system, an orientation of the hand; and
   in response to determining that an orientation difference between the orientation of the hand and a current orientation of the input device is not greater than a threshold orientation difference, causing one or more actuators to move the input device toward the target position.

20. The non-transitory machine-readable medium of claim 19, wherein the method further comprises:
   in response to determining that the orientation difference is not greater than the threshold orientation difference, causing the one or more actuators to move the input device toward a target orientation, wherein moving the input device from the current orientation to the target orientation moves the input device closer to a grasping orientation for the hand.

* * * * *